United States Patent [19]

Tercero et al.

[11] Patent Number: 5,990,165
[45] Date of Patent: Nov. 23, 1999

[54] PHARMACEUTICAL COMPOUNDS

[75] Inventors: Concepción Pedregal Tercero; Almudena Rubio Esteban, both of Madrid, Spain

[73] Assignee: Lilly, S.A., Madrid, Spain

[21] Appl. No.: 09/046,445

[22] Filed: Mar. 24, 1998

[30] Foreign Application Priority Data

Mar. 25, 1997 [ES] Spain ..................................... 9700642

[51] Int. Cl.$^6$ ................................................. A61K 31/195
[52] U.S. Cl. ........................ 514/561; 514/558; 514/567; 562/443; 562/434; 562/503; 562/502; 562/505; 562/506; 562/504; 562/571; 562/573; 554/110; 554/111
[58] Field of Search ..................... 562/573, 443, 562/434, 503, 502, 505, 506, 509, 571, 563, 561; 514/558, 507, 561; 554/110, 111

[56] References Cited

U.S. PATENT DOCUMENTS 5,589,501 12/1996 Carrera et al. ........................... 514/438

OTHER PUBLICATIONS

Ezquerra J. et al., J. Org. Chem., 1995, 60, 2925.
Moody C. M. et al., Tetrahedron Lett., 1993, 34, 4667.
Escribano A. et al., Bioorg. and Med. Chem. Lett., 1998, 8, 765.
Baldwin J. E. et al., J. Chem. Soc., Chem. Commun. 1987, 153.
Kasai T. et al., Agric. Biol. Chem. 1984, 48(9), 2271.
Ouerfelli O. et al., Synlett, 1993, 409.
Panday, S. K. et al., Tetrahedron Lett. 1994, 35, 6673.
Hon Y. et al., Heterocycles 1990, 31, 191.
Todeschi, N., et al., Journal of the Chemical Society, Perkin Transactions 2, 1996, 1337–1351.
Chemical Abstracts, vol. 90, No. 23, Jun. 4, 1979, abstract No. 187333j.

*Primary Examiner*—Samuel Barts
*Attorney, Agent, or Firm*—Martin A. Hay

[57] ABSTRACT

A pharmaceutical compound of the formula:

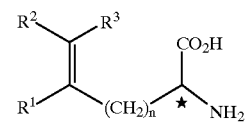

in which n is 1 or 2, $R^1$ is —$CO_2H$, $R^2$ is hydrogen or $C_{1-4}$ alkyl and $R^3$ is hydrogen, $C_{1-10}$ alkyl, $C_{2-10}$ alkenyl, optionally substituted phenyl, optionally substituted phenyl-$C_{1-4}$ alkyl, optionally substituted phenyl $C_{2-10}$ alkenyl, (optionally substituted phenyl)$_2$-$C_{1-4}$ alkyl, optionally substituted $C_{3-7}$ cycloalkyl, optionally substituted $C_{3-7}$ cycloalkyl-$C_{1-4}$ alkyl or optionally substituted $C_{3-7}$ cycloalkyl-$C_{2-10}$ alkenyl, or $R^2$ and $R^3$, together with the carbon atom to which they are attached, form an optionally substituted $C_{4-7}$ cycloalkyl group;

or a salt or ester thereof other than the compounds γ-propylidene-L-glutamic acid, γ-ethylidene-L-glutamic acid and γ-methylidene-L-glutamic acid.

13 Claims, No Drawings

PHARMACEUTICAL COMPOUNDS

This invention relates to novel chemical compounds and their use as pharmaceuticals.

It is well known that excitatory neurotransmission in the mammalian central nervous system is primarily mediated by the amino acid, L-glutamate, acting on ionotropic and metabotropic receptors, and compounds that modify neurotransmission by interaction with these receptors are of interest for their potential use in the treatment of disorders of the central nervous system.

JP 78043519 (Mitsubishi Kasei Kogyo K. K.)discloses the isolation from a fungus of the non-protein amino acids γ-propylidene-L-glutamic acid, γ-ethylidene-L-glutamic acid and γ-methylidene-L-glutamic acid. The activity of the latter compound and some analogs towards glutamate receptors is described in Synlett (June 1993) p 409.

The compounds of the invention have the general formula:

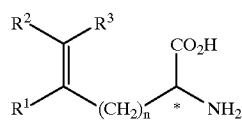

(I)

in which n is 1 or 2, $R^1$ is —$CO_2H$,
$R^2$ is hydrogen or $C_{1-4}$ alkyl and
$R^3$ is hydrogen, $C_{1-10}$ alkyl, $C_{2-10}$ alkenyl, optionally substituted phenyl, optionally substituted phenyl-$C_{1-4}$ alkyl, optionally substituted phenyl $C_{2-10}$ alkenyl,(optionally substituted phenyl)$_2$-$C_{1-4}$ alkyl, optionally substituted $C_{3-7}$ cycloalkyl, optionally substituted $C_{3-7}$ cycloalkyl-$C_{1-4}$ alkyl or optionally substituted $C_{3-7}$ cycloalkyl-$C_{2-10}$ alkenyl, or
$R^2$ and $R^3$, together with the carbon atom to which they are attached, form an optionally substituted $C_{4-7}$ cycloalkyl group;
or a salt or ester thereof other than the compounds γ-propylidene-L-glutamic acid, γ-ethylidene-L-glutamic acid and γ-methylidene-L-glutamic acid.

The compounds of the invention have been found to be active in tests indicative of their use in the treatment of diseases of the central nervous system such as neurological diseases, for example, neurodegenerative diseases, and as antipsychotic, anticonvulsant, analgesic and anti-emetic agents.

In the above general formula, a $C_{1-10}$ alkyl group can be straight or branched chain, such as, for example, methyl, ethyl, propyl, isopropyl, butyl and isobutyl,. A $C_{2-10}$ alkenyl group includes, for example, vinyl, prop-2-enyl, but-3-enyl, pent-4-enyl and isopropenyl, and an alkenyl group can contain more than one double bond and, in addition, one or more triple bonds. A preferred alkenyl group is of the formula R'—CH=CH— where R' is $C_{1-4}$ alkyl.

A $c_{3-10}$ cycloalkyl group is preferably, for example, cyclopropyl, cyclobutyl, cyclopentyl or cyclohexyl and these groups may optionally be substituted by one or two $C_{1-4}$ alkyl, for example methyl, substituents, or can be a bicyclo-system as, for example, bicyclooctane or adamantyl.

In the above general formula, a phenyl group is optionally substituted with, for example, one or more substituents selected from $C_{1-4}$ alkyl, especially methyl, $C_{1-4}$ alkoxy, especially methoxy and ethoxy, carboxy, hydroxy, cyano, halo, especially bromo, chloro and fluoro, trifluoromethyl, nitro, amino (including alkyl substituted amino), $C_{1-4}$ acylamino and $C_{1-4}$ alkylthio. When substituted, a phenyl is preferably substituted by one to three substituents. It is preferred that n is 1.

A preferred group of compounds according to formula (I) is one in which n is 1, $R^1$ is —$CO_2H$, $R^2$ is hydrogen and $R^3$ is $C_{3-4}$ alkyl,or branched alkyls such as isopropyl or $R^2$ and $R^3$ together with the carbon atom to which they are attached form an optionally substituted $C_4$ or $C_5$ cycloalkyl.

A preferred subgroup is one in which $R^2$ is hydrogen and $R^3$ is $C_{1-4}$ alkyl.

Particularly preferred compounds are
(2S,E,E)-2-Amino-4-(p-nitrocinnamylidene)pentanedioic acid
(2S,E,E)-2-Amino-4-(p-dimethylaminocinnamylidene) pentanedioic acid
(2S,E,E)-2-Amino-4-cinnamylidenepentanedioic acid
(2S,E)-2-Amino-4-pentylidenepentanedioic acid
(2S)-2-Amino-4-isopropylidenepentanedioic acid
(2S)-2-Amino-4-cyclobutylidenepentanedioic acid
(2S,E)-2-Amino-4-(p-chlorophenylmethylidene) pentanedioic acid
(2S)-2-Amino-4-cyclohexylidenepentanedioic acid
(2S,E)-2-Amino-4-cyclopentylmethylidenepentanedioic acid and
(2S)-2-Amino-4-cyclopentylidenedioic acid.

It will also be understood that salts of the compounds of the invention can be prepared and such salts are included in the invention. They can be any of the well known base or acid addition salts. Examples of base salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, lithium hydroxide, calcium hydroxide, methylamine, diethylamine, ethylene diamine, cyclohexylamine and ethanolamine. The potassium and sodium salt forms are particularly preferred.

Acid addition salts are preferably the pharmaceutically-acceptable, non-toxic addition salts with suitable acids, such as those with inorganic acids, for example hydrochloric, hydrobromic, nitric, sulphuric or phosphoric acids, or with organic acids, such as organic carboxylic acids, for example glycollic, maleic, fumaric, malic, tartaric, citric, salicylic or o-acetoxybenzoic acids, or organic sulphonic acids, methane sulphonic, 2-hydroxyethane sulphonic, toluene-p-sulphonic or naphthalene-2-sulphonic acids.

In addition to pharmaceutically-acceptable salts, other salts are included in the invention. They may serve as intermediates in the purification of compounds or in the preparation of other, for example pharmaceutically-acceptable, salts, or are useful for identification, characterisation or purification.

The compounds can also be utilised in ester form, such esters being aliphatic or aromatic, such as, for example, alkyl and phenolic esters. The most preferred esters are alkyl esters derived from $C_{1-4}$ alkanols, especially methyl and ethyl esters.

It will be appreciated that the compounds of the invention contain an asymmetric carbon atom as indicated by the asterisk in formula (I), and this gives rise to enantiomers. The preferred stereochemistry for the compunds is the 2S enantiomer. The compounds can be prepared as racemates or as enantiomers, and individual enantiomers can be isolated from racemates by conventional techniques if so desired. Such racemates and individual enantiomers form part of the present invention.

It will also be appreciated that the compounds of the invention contain a double bond and this gives rise to geometric isomers (E, Z), both of which are included in the invention.

The invention also includes a process for the production of compounds of the invention, which comprises hydrolysing a compound of the formula:

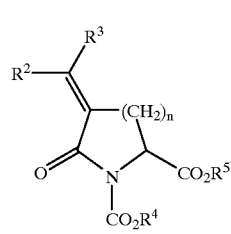

(II)

where $R^4$ and $R^5$ are each carboxy protecting groups, to give a compound of formula (I).

The reaction described in process variant (1) is one of hydrolysis under conventional hydrolysis conditions using acid and/or base. Hydrolysis results in the opening up of the cyclic structure, and the loss of protecting groups. Preferably the reaction is carried out at room temperature, in an organic solvent such as, for example tetrahydrofuran with, for example, aqueous lithium hydroxide. Removal of protecting groups can be carried out with, for example, saturated hydrochloric acid in ethyl acetate.

Novel intermediate compounds of formula (II) are included as part of the present invention and can be prepared by the action of base on a mesylate derivative of formula:

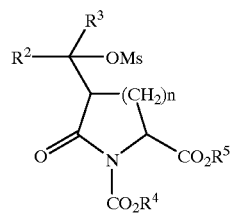

(III)

where Ms is mesylate, which leads to the formation of the unsaturated side-chain (it would be understood that other leaving groups such as tosylate, brosylate and halogens, would also be suitable). Compounds of formula (III) are prepared by mesylation of the corresponding hydroxy compound formed by reaction of the appropriate ketone or aldehyde of the formula $R^2COR^3$, with the pyroglutamate derivative of the formula:

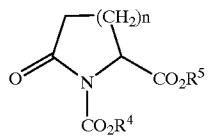

in the presence of strong base such as lithium hexamethyldisilazide, which facilitates the reaction with the ring carbon atom.

According to a further aspect of the invention the compounds described above have pharmaceutical activity. They have been shown to possess affinity for glutamate receptors. Excitatory amino acid or glutamate receptors are subdivided into two types, ionotropic and metabotropic. Ionotropic glutamate receptors are intrinsic ligand gated ion channels that are composed of multiple subunit proteins forming multimeric complexes. Ionotropic glutamate receptors are selectively activated by the agonists N-methyl-D-asparate, AMPA, and kainate (Sommer B. And Seeburg P. H., Trends Pharmacol. Sci. 13: 291–296, 1993). Metabotropic glutamate receptors are a family of G-protein coupled receptors with novel molecular structure that are coupled to increases in phosphoinositide hydrolysis and decreases in cAMP formation. (Schoepp D. D. And Conn J. P., Trends Pharmacol. Sci. 14: 13–20, 1993).

The affinity of the compounds for ionotropic glutamate receptors has been demonstrated by binding assays in which cell membranes are incubated in the presence of radio-ligand [$^3$H]kainate and test compounds prior to separation by centrifugation (see U.S. Pat. No. 5,547,855). The compounds of the present invention are selective agonists of the iGluR5 kainate subreceptor with Ki values of less than 1000 μM.

The compounds of the invention are thus indicated for use in the treatment of neurological disorders such as acute neurodegenerative diseases, for example stroke, cerebral ischemia and head and spinal cord trauma, and chronic neurodegenerative diseases such as, for example, Alzheimer's disease, Parkinson's disease, Amyotropic lateral sclerosis, AIDS-induced dementia and Huntington's Chorea. The compounds are also indicated for use as antipsychotic, anticonvulsant, analgesic and anti-emetic agents. They are also of potential use as anxiolytic and antidepressant agents.

The invention also includes a pharmaceutical composition comprising a pharmaceutically-acceptable diluent or carrier in association with a compound of formula (I), or a pharmaceutically-acceptable salt thereof.

The compounds may be administered by various routes, for example, by the oral or rectal route, topically or parenterally, for example by injection, and are usually employed in the form of a pharmaceutical composition. Such compositions form part of the present invention and are prepared in a manner well known in the pharmaceutical art and normally comprise at least one active compound in association with a pharmaceutically-acceptable diluent or carrier. In making the compositions of the present invention, the active ingredient will usually be mixed with a carrier, or diluted by a carrier, and/or enclosed with a carrier which may, for example, be in the form of a capsule, sachet, paper or other container. Where the carrier serves as a diluent, it may be a solid, semi-solid, or liquid material which acts as a vehicle, excipient or medium for the active ingredient. Thus, the composition may be in the form of tablets, lozenges, sachets, cachets, elixirs, suspensions, as a solid or in a liquid medium, ointments containing, for example, up to 10% by weight of the active compound, soft and hard gelatin capsules, suppositories, injection solutions and suspensions and sterile packaged powders.

Some examples of suitable carriers are lactose, dextrose, sucrose, sorbitol, mannitol, starches, gum acacia, calcium phosphate, alginates, tragacanth, gelatin, syrup, methyl cellulose, methyl- and propyl-hydroxbenzoate, talc, magnesium stearate and mineral oil. Compositions in injectable form may, as it is well known in the art, be formulated so as to provide quick, sustained or delayed release of the active ingredient after administration to the patient.

When the compositions are formulated in unit dosage form, it is preferred that each unit dosage form contains from 5 mg to 500 mg, for example, from 15 mg to 200 mg. The term 'unit dosage form' refers to physically discrete units suitable as unit dosages for human subjects and animals.

Each unit contains a predetermined quantity of active material calculated to produce the desired therapeutic effect, in association with the required pharmaceutical carrier.

The active compounds are effective over a wide dosage range and, for example, dosages per day will normally fall within the range of from 0.5 to 300 mg/kg, more usually in the range of from 5 to 100 mg/kg. However, it will be understood that the amount administered will be determined by the physician in the light of the relevant circumstances, including the condition to be treated, the choice of compound to be administered and the chosen route of administration, and therefore the above dosage ranges are not intended to limit the scope of the invention in any way.

The invention is illustrated by the following Examples.

EXAMPLE 1

Procedure A

General procedure for aldol reactions on ethyl N-Boc pyroglutamate and further treatment of the resulting aldols mixtures with methanesulfonyl chloride and triethylamine. Synthesis of 4-alkylidene pyroglutamates.

To a solution of ethyl N-Boc pyroglutamate (15.6 mmol) in THF (50 mL) stirred at −78° C. was added a 1M solution of lithium hexamethyldisilazide in THF (18.7 mL, 18.7 mmol, 1.1 equiv). The reaction mixture was stirred for 1 hour at −78° C. prior to the addition of a solution of the aldehyde (17.2 mmol) and $BF_3OEt_2$ (17.2 mmol) in THF (50 mL). The reaction mixture was stirred for 1 hour at −78° C. and then quenched with saturated ammonium chloride solution (100 mL) and extracted with ethyl ether (3×50 mL). The combined organic phases were dried over $Na_2SO_4$, filtered and evaporated to dryness. The reaction crude was dissolved in $CH_2Cl_2$ (30 mL) and treated with methanesulfonyl chloride (1.34 mL, 17.2 mmol) and triethylamine (18 mL, 172 mmol). After stirring this solution for three days at room temperature it was quenched with water and extracted with dichloromethane (3×50 mL). The organic layer was dried over $Na_2SO_4$ and evaporated under reduced pressure affording the title compounds as mixtures of E/Z isomers. The eluent is indicated in the cases where chromatographic separation was carried out.

Ethyl (2S, E)-1-(tert-butoxycarbonyl)-4-anthrylmethylidenepyroglutamate

Only the E isomer was obtained. Yellow solid. m.p.: 62–3° C. (Hexane/ethyl acetate 3:1). $[\alpha]_D$=+10.6° (c 0.6, $CHCl_3$). IR (KBr pellet) 2975, 1780, 1740, 1310, 1145 $cm^{-1}$. $^1$HNMR ($CDCl_3$) d 8.47 (S, 1H), 8.44 (t, J=3.1 Hz, 1H), 8.07–8.02 (m, 2H), 7.94–7.88 (m, 2H), 7.54–7.45 (m, 4H), 4.59 (dd, J=3.1 and 10.0 Hz, 1H), 4.20–4.07 (m, 2H), 2.76 (ddd, J=3.1, 10.0 and 18.0 Hz, 1H), 2.28 (dt, J=3.1 and 18.0 Hz, 1H), 1.57 (s, 9H), 1.20 (t, J=7.0 Hz, 3H). $^{13}$C NMR ($CDCl_3$) d 170.8, 165.6, 149.8, 134.0, 138.2, 131.0, 128.9 (3C), 128.4 (2C), 127.8 (2C), 126.2 (2C), 125.3 (2C), 124.9 (2C), 83.6, 61.5, 55.8, 27.8 (3C), 27.1, 13.9. HRMS calcd for $C_{27}H_{27}NO_5$: 445.1889, found 445.1887.

(2S, E)-1-(tert-Butoxycarbonyl)-4-(4,4-diphenylbutylidene) pyroglutamate ethyl ester (hexane/ethyl acetate 4:1).

Colourless oil. $[\alpha]_D$=+3.4° (c 1.0, $CHCl_3$). $^1$H NMR ($CDCl_3$). d 7.40–7.05 (m, 10H), 6.73 (tt, J=2.8 and 7.4 Hz, 1H), 4.51 (dd, J=3.6 and 10.3 Hz, 1H), 4.19 (q, J=7.1 Hz, 2H), 3.85 (t, J=7.7 Hz, 1H), 2.82–2.58 (m, 1H), 2.42–2.00 (m, 5H), 1.49 (S, 9H), 1.25 (t, J=7.1 Hz, 3H). $^{13}$C NMR ($CDCl_3$) d 170.6, 165.3, 149.3, 143.6, 143.5, 137.8, 128.0 (2C), 127.2 (2C), 127.1 (2C), 125.8, 82.7, 61.0, 55.2, 53.1, 49.8, 33.2, 27.3, 27.0, 24.7, 13.6. IR (film) 1784, 1748, 1717, 1317, 1155 $cm^{-1}$.

(2S, Z)-1-(tert-Butoxycarbonyl)-4-(4,4-diphenylbutylidene) pyroglutamate ethyl ester (hexane/ethyl acetate 4:1).

Colourless oil. $[\alpha]_D$=−14.0° (c 1.0, $CHCl_3$). $^1$H NMR ($CDCl_3$) d 7.38–7.05 (m, 10H), 5.94 (m, 1H), 4.46 (dd, J=3.4 and 10.0 Hz, 1H), 4.16 (q, J=7.1 Hz, 2H), 3.92 (t, J=7.7 Hz, 1H), 2.95–2.63 (m, 3H), 2.45 (m, 1H), 2.14 (q, J=7.7 Hz, 2H), 1.48 (S, 9H), 1.21 (t, J=7.1 Hz, 3H). $^{13}$C NMR ($CDCl_3$) d 170.8, 165.2, 149.6, 144.3, 144.2, 142.5, 128.0, 127.5 (2C), 127.4 (2C), 126.2, 125.7, 82.8, 61.1, 55.4, 50.8, 34.7, 28.6, 27.5, 25.6, 13.7. IR (film) 1784, 1747, 1717, 1323, 1155 $cm^{-1}$.

Ethyl (2S)-1-(tert-butoxycarbonyl)-4-(4-chlorobenzylidene) pyroglutamate white solid. P.f.: 114–118° C. $[a]_D^{20}$: 6.2.

$^1$H-RMN ($CDCl_3$): 7.37 (m, 1H, C=CH); 7.14 (m, 4H, Ar-H); 4.59 (dd, 1H, J=9.7 y 3.2 Hz, H-γ); 4.09 (c, 2H, J=7.0 Hz, $CH_2$-Et); 3.21 (ddd, J=17.7, 10.2 y 2.7 Hz, H-β); 2.81 (dm, 1H, J=17.7, H-β); 1.41 (s, 9H, $CH_3$-Boc); 1.15 (t, 3H, J=7.0 Hz, $CH_3$-Et). $^{13}$C-RMN ($CDCl_3$): 171.0 y 166.6 (CON y $CO_2Et$); 149.8 (N$CO_2^tBu$); 133.1, 128.6 y 127.8 (C); 133.8, 131.2 y 129.2 (CH); 127.8 (ArC-Cl); 83.8 (C-Boc); 61.9 ($CH_2$-Et); 56.1 (C-γ); 27.9($CH_3$-Boc); 14.1 ($CH_3$-Et). IR ($cm^{-1}$): 1775 y 1745 (st, C=O); 1660 (st, C=C); 1385 y 1375 (d, $CH_3$-Boc); 835 y 775 (d, ArC-H). MS: 379 (0.4, $M^+$); 297 (30); 208 (44); 206 (100); 178 (10); 56 (47).

Ethyl (2S)-1-(tert-butoxycarbonyl)-4-cyclopentylmethylidenepyroglutamate

Colourless oil $^1$H-RMN ($CDCl_3$): 6.63 (dt, 1H, J=10.0 y 2.0 Hz, CH=C); 4.56 (dd, 1H, J=10.0 y 3.2 Hz, H-γ); 4.19 (c, 2H, J=7.0 Hz, $CH_2$-Et); 2.96 (ddd, 1H, J=16.4, 10.0 y 3.2 Hz, H-β); 2.50 (m, 2H, H-β y CH-Cp); 1.90–1.20 (m, 8H, $CH_2$); 1.55 (s, 9H, $CH_3$-Boc); 1.25 (t, 3H, J=7.0 Hz, $CH_3$-Et). IR ($cm^{-1}$): 1775 y 1730 (st, C=O); 1670 (st, C=C); 1390 y 1370 (d, $CH_3$-Boc). MS: 237 (34); 186 (9); 164 (100); 96 (11); 81 (34); 57 (39).

Ethyl (2S)-1-(tert-butoxycarbonyl)-4-cyclohexylidenepyroglutamate yellow oil. Isomer A: $^1$H-RMN ($CDCl_3$): 4.48 (dd, 1H, J=10.0 y 3.6 Hz, H-γ); 4.16 (c, 2H, J=7.0 Hz, $CH_2$-Et); 2.95 (m, 1H, H-β) ; 2.55 (dd, 1H, J=15.4 y 3.6 Hz, H-β); 2.10 (m, 4H, $CH_2$); 2.00–1.1 (m, 6H, $CH_2$); 1.5 (s, 9H, $CH_3$-Boc); 1.23 (t, 3H, J=7.0 Hz, $CH_3$-Et). Isomer B: $^1$H-RMN ($CDCl_3$): 5.57 (m, 1H, CH=C); 4.54 (dd, 1H, J=8.9 y 2.3 Hz, H-γ); 4.19 (c, 2H, J=7.0 Hz, $CH_2$-Et); 3.19 (dd, 1H, J=10.2 y 8.9 Hz, H-β); 2.95 (m, 1H, H-β); 2.10 (m, 5H, H-a y $CH_2$); 2.00–1.10 (m, 4H, $CH_2$); 1.55 (s, 9H, $CH_3$-Boc); 1.25 (t, 3H, J=7.0 Hz, $CH_3$-Et). $^{13}$C-RMN ($CDCl_3$): 171.4 y 171.2 (CON, $CO_2Et$); 157.2 (N$CO_2^tBu$); 132.5 (C-a Iso A); 126.7 (CH=C Iso B); 125.4 (C-4 Iso B); 118.0 (C-4 Iso B); 83.0 (C-Boc); 61.4 y 61.3 ($CH_2$-Et); 56.8 (C-γ); 49.7 (C-a Iso B ; 27.7 ($CH_3$-Boc); 33.7, 28.1, 27.0, 26.0, 25.5, 25.1, 22.4, 21.9 ($CH_2$); 14.0 ($CH_3$-Et). IR ($Cm^{-1}$): 1770 y 1720 (st, C=O); 1640 (st, C=C) 1390 y 1370 (d, $CH_3$-Boc) . MS: 237 (100); 164 (88); 136 (38); 121 (25); 107 (27).

Ethyl (2S, E)-N-Boc-[(2,2-dimethyl)-4-cyclopentylidene]pyroglutamate

Oil. $^1$HNMR ($CDCl_3$) 0.93, 1.01 (2s, 6H, 2×$CH_3$), 1.23 (t, 3H, J=7.0 Hz, $CH_3CH_2$), 1.43 (s, 9H, $(CH_3)_3C$), 1.65, 2.17

(2m, 6H, CH$_2$CH$_2$CH$_2$), 3.11 (q, 2H, J=9.6 Hz, CHCH$_2$), 4.18 (t, 2H, J=7.0 Hz, CH$_2$CH$_3$) and 4.5 ppm (dd, 1H, J=2.3, 9.6 Hz, CHCO$_2$Et). m/z 295 (M$^+$−56, 1%), 25 (M$^+$−100, 12), 222 (2), 178 (11), 157 (13), 95 (19), 57 (100) and 41 (19). IR (cm$^{-1}$): 3037 (C≡C), 1792, 1747 and 1717 (C=O).

Ethyl (2S, Z)-N-Boc-[(2,2-dimethyl)-4-cyclopentylidene]pyroglutamate

Oil. $^1$HNMR (CDCl$_3$) 1.05, 1.09 (2s, 6H, 2×CH$_3$), 1.21 (t, 3H, J=7.2 Hz, CH$_3$CH$_2$), 1.43 (s, 9H, (CH$_3$)$_3$C), 1.39–1.70 (m, 5H), 2.6–3.2 (m, 3H), 4.15 (q, 2H, J=7.2 Hz, CH$_2$CH$_3$) and 4.49 ppm (dd, 1H, J=3.8, 9.9 Hz, CHCO$_2$Et). $^{13}$CNMR (CDCl$_3$): 13.97 (CH$_3$CH$_2$), 22.72, 26.35, 33.67 (CH$_2$CH$_2$CH$_2$), 24.85, 25.13 (2×CH$_3$), 27.76 ((CH$_3$)$_3$C), 43.06 (CHCH$_2$), 44.60 ((CH$_3$)$_2$C), 55.77 (CHCO$_2$Et), 61.27 (CH$_3$CH$_2$), 82.77 ((CH$_3$)$_3$CO), 117.35, 150.16 (C=C), 167.10, 167.64 (2×O=CN) and 171.37 ppm (C=O). m/z 295 (M$^+$−56, 2%), 25 (M$^+$−100, 30), 222 (2), 178 (43), 95 (45), 82 (11), 57 (100) and 41 (39). IR (cm$^{-1}$): 1779, 1746 and 1717 (C=O).

Ethyl-(2S, E, E)-N-Boc-4-cinnamylidenepyroglutamate

M.p.: 80–81° C. [α]$_D$=+57.3 (c 1.06, CHCl$_3$). $^1$HMNR (CDCl$_3$): 7.49–7.23 (m, 6H, Ph and HC=), 6.95 (d, 1H, J=15.5 Hz, CH-Ph), 6.78 (dd, 1H, J=11.0 y 15.5 Hz, HC=), 4.68 (dd, 1H, J=10.1 and 3.6 Hz, H-2), 4.30–4.17 (m, 2H, CO$_2$CH$_2$), 3.18 (ddd, 1H, J=18.1, 10.1 and 3.0 Hz), 2.84 (dt, 1H, J=18.1 and 3.0 Hz), 1.52 (s, 9H, C(CH$_3$)$_3$), 1.29 (t, 3H, J=7.1 Hz, CH$_2$CH$_3$). $^{13}$CNMR (CDCl$_3$): 170.5, 165.8, 149.0, 140.4, 135.4, 133.7, 128.5, 128.1 (2C), 127.3, 126.6 (2C), 122.5, 82.5, 60.9, 55.3, 27.2 (3C), 25.4, 13.5. IR (CHCl$_3$): 2995, 1780, 1735, 1310, 1150 cm$^{-1}$. HRMS calcd. for C$_{21}$H$_{25}$NO$_5$: 371.1722 found 371.1732.

Ethyl-(2S, E, E)-N-Boc-4-(o-methoxycinnamylidene)pyroglutamate

EtOAc/hexane 1:4 [α]$_D$=+7.2 (c 1.0, CHCl$_3$). $^1$HNMR (CDCl$_3$): 7.52 (d, 1H, J=7.8 Hz), 7.32–7.22 (m, 3H), 6.95–6.72 (m, 3H), 4.59 (dd, 1H, J=10.4 and 4.1 Hz, H-2), 4.25 (q, 2H, J=7.1 Hz, CO$_2$CH$_2$), 3.87 (s, 3H, OCH$_3$), 3.24–3.10 (m, 1H), 2.72 (dt, 1H, J=18.1 and 2.9 Hz), 1.52 (s, 9H, C(CH$_3$)3), 1.28 (t, 3H, J=7.1 Hz, CH$_2$CH$_3$). $^{13}$CNMR (CDCl$_3$): 171.2, 166.5, 157.3, 149.8, 136.5, 135.6, 130.6, 127.3, 126.7, 124.8, 123.5, 120.5, 110.9, 83.3, 61.6, 55.9, 55.4, 27.8 (3C), 26.0, 14.0. IR (film): 1790, 1770, 1755, 1747, 1371 cm$^{-1}$.

Ethyl-(2S, E, E)-N-Boc-4-(p-nitrocinnamylidene)pyroglutamate

EtOAc/hexane 1:3. M.p.: 162–163° C. [α]$_D$=+48.3 (c 0.6, CHCl$_3$). $^1$HNMR (CDCl$_3$): 8.22 and 7.61 (AA'BB', 4H), 7.32–7.24 (m, 1H), 6.97–6.93 (m, 2H), 4.72 (dd, 1H, J=10.0 and 3.0 Hz, H-2), 4.30–4.19 (m, 2H, CO$_2$CH$_2$), 3.22 (ddd, 1H, J=18.1, 10.0 and 2.8 Hz), 2.89 (dt, 1H, J=18.1 and 2.8 Hz), 1.53 (s, 9H, C(CH$_3$)$_3$), 1.30 (t, 3H, J=7.1 Hz, CH$_2$CH$_3$). $^{13}$CNMR (CDCl$_3$): 170.9, 166.0, 149.6, 147.5, 142.2, 138.0, 132.2, 130.9, 127.6 (2C), 127.1, 124.1 (2C), 83.8, 61.9, 55.9, 27.8 (3C), 26.2, 14.1. IR (KBr): 1784, 1747, 1514, 1336, 1155 cm$^{-1}$.

Benzyl (2S, E, E)-N-Boc-4-(p-dimethylaminocinnamylidene)pyroglutamate

EtOAc/hexane 1:3. M.p.: 136–138° C. [α]$_D$=+175.1 (c 0.7, CHCl$_3$). $^1$HNMR (CDCl$_3$): 7.38–7.21 (m, 4H), 6.81 (d, 1H, J=15.3 Hz, HC=), 6.65 (d, 1H, J=11.6 Hz), 6.54 (dd, 1H, J=15.3 and 11.6 Hz), 5.19 (AB, 2H, CO$_2$CH$_2$), 4.71 (dd, 1H, J=10.2 and 2.5 Hz, H-2), 3.22–3.04 (m, 1H), 3.01 (s, 6H, NMe$_2$), 2.79 (dt, 1H, J=17.7 and 2.7 Hz), 1.44 (s, 9H, C(CH$_3$)$_3$). $^{13}$CNMR (CDCl$_3$): 171.1, 166.8, 150.9, 149.9, 142.2, 136.0, 135.0, 128.7 (2C), 128.6 (2C), 128.5 (2C), 128.4 (2C), 123.9, 116.4, 111.0, 83.2, 67.2, 55.9, 40.1 (2C), 27.7 (3C), 26.1. IR (KBr): 1770, 1601, 1321, 1280, 1149 cm$^{-1}$.

Benzyl (2S, E)-N-Boc-4-pentylidenepyroglutamate

EtOAc/hexane 1:5. [α]$_D$=−13.3 (c 0.3, CHCl$_3$). $^1$HNMR (CDCl$_3$): 7.32 (s, 5H), 6.69 (tt, 1H, J=7.7 and 2.7 Hz, HC=), 5.16 (AB, 2H, CO$_2$CH$_2$), 4.63 (dd, 1H, J=10.2 and 3.5 Hz, H-2), 3.00–2.82 (m, 1H), 2.61–2.49 (m, 1H), 2.12–2.02 (m, 2H), 1.41 (s, 9H, C(CH$_3$)$_3$), 1.37–1.22 (m, 4H), 0.85 (t, 3H, J=7.0 Hz, CH$_2$CH$_3$). $^{13}$CNMR (CDCl$_3$): 171.0, 165.9, 149.8, 139.6, 135.0, 128.6 (2C), 128.5 (2C), 128.4, 128.1, 83.5, 67.2, 55.8, 30.2, 29.1, 27.7 (3C), 25.5, 22.3, 13.7. IR (KBr): 1786, 1746, 1717, 1317, 1155 cm$^{-1}$.

Ethyl (2S)-N-Boc-4-cyclobutylidenepyroglutamate

EtOAc/hexane 1:3. [α]$_D$=−5.0 (c 0.4, CHCl$_3$). $^1$HNMR (CDCl$_3$): 4.55 (dd, 1H, J=10.3 and 3.7 Hz, H-2), 4.26–4.10 (m, 2H, CO$_2$CH$_2$), 3.21–3.12 (m, 2H), 2.91–2.68 (m, 3H), 2.49–2.35 (m, 1H), 2.20–1.83 (m, 2H), 1.48 (s, 9H, C(CH$_3$)$_3$), 1.24 (t, 3H, J=7.1 Hz, CH$_2$CH$_3$). $^{13}$CNMR (CDCl$_3$): 171.5, 165.6, 158.9, 150.4, 118.6, 83.2, 61.5, 55.8, 32.4, 31.5, 27.9 (3C), 25.2, 18.3, 14.1. IR (KBr): 1782, 1743, 1715, 1319, 1153 cm$^{-1}$.

Benzyl(2S)-1-(tert-butoxycarbonyl)-4-(2-methylpropylidene)pyroglutamate

A 85:15 mixture of E/Z isomers was obtained. The diastereomers were separated by chromatography (hexane/ethyl acetate 3:1). For the E isomer: Oil. $^1$HNMR (CDCl$_3$) d 7.30 (S, 5H), 6.50 (dt, 1H, HC=), 5.15 (AB, 2H, CO$_2$CH$_2$), 4.60 (dd, 1H, H-2), 3.00–2.80 (m, 1H), 2.60–2.30 (m, 2H), 1.50 (s, 9H, C(CH$_3$)$_3$), 1.00 (d, 3H), 0.95 (d, 3H). $^{13}$C NMR (CDCl$_3$) d 171.0, 166.4, 149.8, 145.8, 134.9, 126.6, 126.4, 125.9, 83.6, 67.2, 55.9, 29.0, 28.1, 27.7, 25.3, 21.6, 21.4

For the Z isomer: Oil. $^1$HNMR (CDCl$_3$) d 7.30 (S, 5H), 5.30 (dt, 1H, HC=), 5.2 (s, 2H, CO$_2$CH$_2$), 3.17 (dd, 1H), 3.21 (m, 1H), 3.19 (m, 1H), 3.75 (m, 1H), 1.40 (s, 9H), 1.00 (d, 3H), 0.95 (d, 3H)

Benxyl (2S)-1-(tert-butoxycarbonyl)-4-(3-methylbutylidene)pyroglutamate

A 85:15 mixture of E/Z isomers was obtained. The diastereomers were separated by chromatography (hexane/ethyl acetate 3:1). For the E isomer: Oil. $^1$HNMR (CDCl$_3$) d 7.35 (s, 5H), 6.70 (m, 1H, HC=), 5.15 (AB, 2H, CO$_2$CH$_2$), 4.60 (dd, 1H, H-2), 3.00–2.50 (m, 2H), 2.00–1.60 (m, 3H), 1.50 (S, 9H, C(CH$_3$)$_3$), 0.90 (d, 3H), 0.80 (d, 3H). $^{13}$C NMR (CDCl$_3$) d 170.9, 165.8, 149.8, 138.4, 134.9, 128.8, 128.5, 128.4, 128.3, 83.3, 67.1, 55.7, 38.3, 27.9, 27.6, 25.6, 22.2.

Benzyl(2S)-1-(tert-butoxycarbonyl)-4-(3-phenylpropylidene)pyroglutamate

A 85:15 mixture of E/Z isomers was obtained. The diastereomers were separated by chromatography (hexane/ethyl acetate 3:1). For the E isomer: Oil. $^1$HNMR (CDCl$_3$) d 7.35–7.10 (m, 10H), 6.70 (m, 1H, HC=), 5.15 (AB, 2H, $CO_2CH_2$), 4.55 (dd, 1H, H-2), 2.80–2.30 (m, 4H), 1.40 (S, 9H, $C(CH_3)_3$). $^{13}C$ NMR ($CDCl_3$) d 170.4, 165.2, 149.2, 140.1, 137.6, 134.6, 128.7, 128.0, 125.4, 82.8, 66.6, 55.4, 33.6, 30.8, 26.1.

Benzyl(2S)-1-(tert-butoxycarbonyl)-4-diethylmethylidene)pyroglutamate

Oil. $^1HNMR$ ($CDCl_3$) d 7.3 (S, 5H), 5.20 (S, 2H, $CO_2CH_2$), 4.55 (dd, 1H, H-2), 3.00–2.50 (m, 4H), 2.20–2.00 (m, 3H), 1.50 (S, 9H, $C(CH_3)_3$), 1.10–0.90 (m, 6H).

Benzyl(2S)-1-(tert-butoxycarbonyl)-4-(2,2-dimethylpropylidene)pyroglutamate

Oil. 1HNMR ($CDCl_3$) d 7.35 (S, 5H), 6.60 (m, 1H), 5.20 (S, 2H, $C_2CH_2$), 4.55 (dd, 1H, H-2), 3.20–2.65 (m, 2H), 1.50 (s, 9H, $C(CH_3)_3$). 1.10 (s, 9H).

Ethyl (2S, E)-1-(tert-butoxycarbonyl)-4-propylidenepyroglutamate

A 92:8 mixture of E/Z isomers was obtained. Isolation of the minor isomer was not possible. Pure E isomer was isolated by column chromatography (hexane/ethyl acetate 4:1). Oil. 70% yield $[a]_D=-11.30°$ (c 0.76, $CHCl_3$). IR ($CHCl_3$) 3010, 1780, 1735, 1315, 1155 $cm^{-1}$.$^1HNMR$ ($CDCl_3$) d 6.71 (tt, J=2.9 and 7.5 Hz, 1H), 4.61 (dd, J=3.7 and 10.1 Hz, 1H), 4.22 (q, J=7.2 Hz, 2H), 3.04–2.88 (m, 1H), 2.66–2.53 (m, 1H), 2.23–2.07 (m, 2H), 1.51 (s, 9H), 1.28 (t, J=7.2 Hz, 3H), 1.06 (t, J=7.5 Hz, 3H). $^{13}C$ NMR ($CDCl_3$) d 171.2, 165.9, 149.9, 140.6, 127.8, 83.3, 61.5, 55.8, 27.8 (3C), 25.4, 22.7, 14.0, 12.5. HRMS calcd for $C_{10}H_{15}NO_3$ [M+-$CO_2C(CH_3)_3$+1]: 197.1052, found 197.1046.

Benzyl (2S, E)-N-Boc-4-pentylidenepyroglutamate

36% Yield. EtOAc/hexane 1:5. $[\alpha]_D=-13.3$ (c 0.3, $CHCl_3$).$^1HNMR$ ($CDCl_3$) d 7.32 (s, 5H), 6.69 (tt, 1H, J=7.7 and 2.7 Hz, HC=), 5.16 (AB, 2H, $CO_2CH_2$), 4.63 (dd, 1H, J=10.2 and 3.5 Hz, H-2), 3.00–2.82 (m, 1H), 2.61–2.49 (m, 1H), 2.12–2.02 (m, 2H), 1.41 (s, 9H, $C(CH_3)_3$), 1.37–1.22 (m, 4H), 0.85 (t, 3H, J=7.0 Hz, $CH_2CH_3$). $^{13}CNMR$ ($CDCl_3$) d 171.0, 165.9, 149.8, 139.6, 135.0, 128.6 (2C), 128.5 (2C), 128.4, 128.1, 83.5, 67.2, 55.8, 30.2, 29.1, 27.7 (3C), 25.5, 22.3, 13.7. IR (KBr): 1786, 1746, 1717, 1317, 1155 $cm^{-1}$.

Benzyl(2S)-1-(tert-butoxycarbonyl)-4-(2-methylpropylidene)pyroglutamate

A 85:15 mixture of E/Z isomers was obtained. The diastereomers were separated by chromatography (hexane/ethyl acetate 3:1). 70% yield. For the E isomer: Oil. $^1HNMR$ ($CDCl_3$) d 7.30 (s, 5H), 6.50 (dt, 1H, HC=), 5.15 (AB, 2H, $CO_2CH_2$), 4.60 (dd, 1H, H-2), 3.00–2.80 (m, 1H), 2.60–2.30 (m, 2H), 1.50 (s, 9H, $C(CH_3)_3$), 1.00 (d, 3H), 0.95 (d, 3H). $^{13}C$ NMR ($CDCl_3$) d 171.0, 166.4, 149.8, 145.8, 134.9, 126.6, 126.4, 125.9, 83.6, 67.2, 55.9, 29.0, 28.1, 27.7, 25.3, 21.6, 21.4.

For the Z isomer: Oil. $^1HNMR$ ($CDCl_3$) d 7.30 (s, 5H), 5.30 (dt, 1H, HC=), 5.2 (s, 2H, $CO_2CH_2$), 3.17 (dd, 1H), 3.21 (m, 1H), 3.19 (m, 1H), 3.75 (m, 1H), 1.40 (s, 9H), 1.00 (d, 3H) , 0.95 (d, 3H).

Benzyl(2S)-1-(tert-butoxycarbonyl)-4-(2,2-dimethylpropylidene)pyroglutamate

Oil. $^1HNMR$ ($CDCl_3$) d 7.35 (s, 5H), 6.60 (m, 1H), 5.20 (s, 2H, $CO_2CH_2$), 4.55 (dd, 1H, H-2), 3.20–2.65 (m, 2H), 1.50 (s, 9H, $C(CH_3)_3$), 1.10 (s, 9H).

Benzyl (2S, 4E, 6E)-N-Boc-(2-butadienylene) pyroglutamate: Oil; $[\alpha]D=+9.7$ (c 2, CHCl3). 1H NMR (CHCl3) 7.24 (s, 5H), 6.80 (d, J=8.0 Hz, 1H), 6.00 (m, 2H), 5.05 (m, 2H), 4.58 (dd, J=3.5 and 10.3 Hz, 1H), 2.95 (m, 1H), 2.60 (m, 1H), 1.77 (d, J=6.0 Hz, 3H), 1.33 (s, 9H).13C NMR (CHCl3) 170.7, 166.4, 149.4, 140.2, 134.7, 134.5, 128.2, 128.1,127.9, 126.8, 126.5, 83.0, 66.9, 55.6, 27.4, 25.5, 18.7. IR (film) 3050,1780, 1750, 1650, 1300, 1150 cm-1.

Procedure B

General procedures for the hydrolysis of 4-substituted N-BOC pyroglutamate ethyl esters. Synthesis of γ-alkyl glutamic acid hydrochlorides:

To a solution of the title compounds (2 mmol) in THF (15 mL) was added a 2.5 N aqueous solution of LiOH (14.4 mL, 36 mmol). The mixture was stirred at room temperature for four hours, then acidified to pH 2 with 1N HCl solution and extracted with ethyl ether (3×20 mL). The combined organic layers were dried over $Na_2SO_4$ and concentrated in vacuo to give an oily residue which was reacted with a saturated HCl solution in ethyl acetate for one hour at room temperature. The resulting white solid was triturated with ethyl ether (3×20 mL). The final amino acids were isolated either as hydrochlorides or as zwitterions by treatment of a methanolic solution of the hydrochloride with propylene oxide.

(2S, E)-4-Propylideneglutamic acid $[\alpha]_D=+11°$ (c 0.5, 3N HCl). $^1H$ NMR ($D_2O$) d 6.88 (t, J=7.6 Hz, 1H), 3.67 (dd, J=6.1 and 7.7 Hz, 1H), 2.80–2.57 (m, 2H), 2.09 (quintet, J=7.6 Hz, 2H), 0.87 (t, J=7.6 Hz, 3H). $^{13}C$ NMR ($D_2O$) d 182.8, 177.4, 141.0, 133.3, 57.4, 35.3, 22.8, 14.3.

(2S,E,E) -2-Amino-4-(p-nitrocinnamylidene)pentanedioic acid

M.p.: >200 C. $[\alpha]_D=+10.0$ (c 0.1, 6N HCl).$^1HNMR$ (MeOH-$d_4$/KOD):8.20 and 7.79 (AA'BB', 4H), 7.52 (dd, 1H, J=15.3 and 11.4 Hz, HC=), 7.22 (d, 1H, J=11.4 Hz, HC=), 6.87 (d, 1H, J=15.3 Hz, HC=), 3.40 (dd, 1H, J=8.1 and 4.6 Hz, H-2), 3.02 (dd, 1H J=12.8 and 4.6 Hz), 2.75 (dd, 1H, J=12.8 and 8.1 Hz). $^{13}CNMR$ (MeOH-$d_4$/KOD): Decomposes in solution 183.3, 177.3, 147.6, 145.0, 138.6, 137.1, 136.0, 130.0, 128.6 (2C), 125.2 (2C), 57.3, 35.2. IR (KBr): 1649, 1608, 1531, 1344 $cm^{-1}$.

(2S,E,E)-2-Amino-4-(p-dimethylaminocinnamylidene)pentanedioic acid

M.p.: 195–196 C. $[\alpha]_D=+44.7$ (c 0.4, 1N HCl).$^1HNMR$ (MeOH-$d_4$/KOD): 7.40 and 6.74 (AA'BB', 4H), 7.25 (d, 1H, J=11.2 Hz, HC=), 7.00 (dd, 1H, J=15.1 and 11.2 Hz, HC=), 6.73 (d, 1H, J=15.1 Hz, HC=), 3.36 (dd, 1H, J=9.3 and 4.6 Hz, H-2), 2.92 (s, 6H, $NMe_2$), 2.96–2.88 (m, 1H), 2.63 (dd, 1H J=12.7 and 9.3 Hz). $^{13}CNMR$ (MeOH-$d_4$/KOD): 183.1, 177.4, 152.1, 139.1, 138.8, 134.0, 129.2, 127.1, 127.7, 114.1, 57.7, 41.0. IR (KBr): 1668, 1597, 1358, 1159 $cm^{-1}$.

(2S,E,E)-2-Amino-4-cinnamylidenepentanedioic acid

M.p.: 198 C (dec). $^1HNMR$ ($D_2O$/KOD): 7.01–6.86 (m, 2H), 6.80–6.71 (m, 2H), 6.80–6.71 (m, 2H), 6.52 (m, 2H), 2.90 (dd, 1H, J=9.2 and 3.9 Hz, H-2), 2.44 (dd, 1H, J=12.8 and 3.9 Hz), 2.22 (dd, 1H J=12.8 and 9.2 Hz). $^{13}CNMR$ ($D_2O$/MeOH-$d_4$/KOD): 183.5, 177.8, 138.6, 138.1, 137.9, 135.8, 130.1 (2C), 129.6, 128.0 (2C), 125.8, 57.3, 34.9. IR (KBr): 1678, 1624, 1439, 1167 $cm^{-1}$.

(2S,E)-2-Amino-4-pentylidenepentanedioic acid

M.p.: 173–175 C. $[\alpha]_D$=+37.0 (c 0.2, 1N HCl). $^1$HNMR (MeOH-d$_4$/KOD): 6.52 (t, 1H, J=7.4 Hz, HC=), 3.30 (m, 1H, H-2), 2.74 (dd, 1H, J=13.2 and 4.7 Hz), 2.44 (dd, 1H J=13.2 and 9.1 Hz), 2.18 (m, 2H), 1.36 (m, 4H), 0.88 (m, 3H). $^{13}$CNMR (MeOH-d$_4$/KOD): 182.8, 177.4, 139.5, 136.9, 57.4, 35.4, 32.7, 29.3, 23.5, 14.5. IR (KBr): 2957, 1713, 1688, 1636 cm$^{-1}$.

(2S)-2-Amino-4-cyclobutylidenepentanedioic acid

M.p.: 212–214 C. $[\alpha]_D$=+5.0 (c 0.2, 1N HCl). $^1$HNMR (MeOH-d$_4$/KOD): 3.27 (dd, 1H, J=8.9 and 4.2 Hz, H-2), 3.00 (q, 2H, J=7.2 Hz), 2.77 (t, 2H, J=7.6 Hz), 2.59 (dd, 1H, J=13.2 and 4.2 Hz), 2.20 (dd, 1H J=13.2 and 8.9 Hz), 1.93 (quintuplet, 2H, J=7.6 Hz). $^{13}$CNMR (MeOH-d$_4$/KOD): 183.0, 176.9, 152.2, 128.8, 57.2, 36.8, 34.0, 31.7, 17.7. IR (KBr): 2915, 1663, 1632, 1595, 1308 cm$^{-1}$.

(2S,E)-2-Amino-4-(p-chlorophenylmethylidene)pentanedioic acid

M.p.: 215 C (dec). $[\alpha]_D$=+32.9 (c 0.1, 1N HCl). $^1$HNMR (MeOH-d$_4$/KOD): 7.36 (AA'BB', 4H), 3.43 (dd, 1H, J=8.6 and 5.6 Hz, H-2), 2.93 (dd, 1H, J=13.4 and 5.6 Hz), 2.68 (dd, 1H, J=13.4 and 8.6 Hz). $^{13}$CNMR (MeOH-d$_4$/KOD): 183.5, 177.2, 140.6, 137.2, 134.4, 134.0, 131.9 (2C), 129.5 (2C), 57.3, 36.0. IR (KBr): 1697, 1651, 1493, 1093 cm$^{-1}$.

(2S)-2-Amino-4-cyclohexylidenepentanedioic acid

Mixture of regioisomers (2:1). $^1$HNMR (MeOH-d$_4$/KOD): 5.58 (bs, 1H, HC=), 3.24 (dd, 1H, J=10.2 and 3.5 Hz, H-2), 3.15 (dd, 1H, J=9.0 and 4.3 Hz), 2.92 (dd, 1H, J=9.7 and 4.5 Hz), 2.72 (dd, 1H, J=13.8 and 3.5 Hz), 2.42 (dd, 1H, J=13.8 and 10.2 Hz), 2.20 (m, 5H), 2.02 (m, 2H), 1.55 (m, 10H). $^{13}$CNMR (MeOH-d$_4$/KOD): 185.5, 182.7, 182.4, 180.8, 139.3, 137.6, 131.3, 122.9, 57.2, 56.8, 55.5, 39.0, 37.2, 34.2, 30.8, 29.3, 29.1, 27.9, 26.4, 24.2, 23.6. IR (KBr): 2955, 1686, 1339 cm$^{-1}$.

(2S,E)-2-Amino-4-cyclopentylmethylidenepentanedioic acid

M.p.: 173–175 C. $[\alpha]_D$=+23.0 (c 0.1, 1N HCl). $^1$HNMR (MeOH-d$_4$/KOD): 6.45 (d, 1H, J=10.0 Hz, HC=), 3.28 (m, 1H, H-2), 2.83 (m, 1H), 2.78 (dd, 1H, J=13.4 and 4.8 Hz), 2.45 (dd, 1H, J=13.4 and 9.3 Hz), 1.87–1.58 (m, 6H), 1.37–1.22 (m, 2H). $^{13}$CNMR (MeOH-d$_4$/KOD): 182.7, 177.5, 144.6, 135.2, 57.5, 40.4, 35.6, 34.6 (2C), 26.6 (2C). IR (KBr): 2928, 1705, 1658, 1604, 1400 cm$^{-1}$.

(2S)-2-Amino-4-isopropylidenepentanedioic acid

M.p.: 198–199° C. $[\alpha]_D$=+24.5 (c 0.2, 1N HCl). $^1$H NMR (MeOH-d$_4$/KOD) 3.26 (dd, 1H, J=9.6 and 3.8 Hz, H-2), 2.54 (dd, 1H, J=13.7 and 3.8 Hz), 2.43 (dd, 1H J=13.7 and 9.6 Hz), 1.80 (s, 3H, CH$_3$), 1.70 (s, 3H, CH$^3$). $^{13}$C NMR (MeOH-d$_4$/KOD) 182.7, 180.7, 134.3, 130.4, 57.2, 38.1, 23.1, 20.2. IR (KBr) 1717, 1657, 1605, 1408, 1202 cm$^{-1}$.

(2S)-2-Amino-4-carboxy-5-ethylhept-4-enoic acid $^1$H NMR (MeOH-KOD) 3.00 (m, 1H), 2.45 (m, 1H), 2,20–1,70 (m, 5H), 0.70 (m, 6H). $^{13}$C NMR (MeOH-KOD) 182.7, 180.6, 140.5, 134.1, 57.0, 37.8, 27.4, 23.9, 14.0, 13.7.

(2S,4E)-2-Amino-4-carboxy-7-phenylhept-4-enoic acid $[\alpha]_D$=+3.1 (c 0.35, Py). $^1$H NMR (D$_2$O-Pyr-d$^5$) 6.9–6.55 (m, 5H), 6.20 (m, 1H), 3.00 (m, 1H), 2.40–1.85 (m, 6H). $^{13}$C NMR (D$_2$O-Pyr-d$^5$) 175.7, 173.7, 141.3, 141.2, 132.4, 128.2, 128.1, 125.6, 54.4, 33.9, 29.6, 28.7. Anal. (C$_{14}$H$_{17}$NO$_4$.H$_2$O) C, H, N.

(2S,4E)-2-Amino-4-carboxy-5-(2-methylthio)ethylpent-4-enoic acid $[\alpha]_D$=+28.0 (c 1, 1N HCl). $^1$H NMR (D$_2$O-Pyr-d$^5$) 7.04 (t, J=5.7 Hz, 1H), 4.21 (dd, J=3.7 and 8.5 Hz, 1H), 3.28 and 3.11 (part AB of an ABX system, JAB=14.7 Hz, JAX=3.7 Hz and JBX=8.5 Hz), 2.84 (m, 4H), 2.37 (s, 3H). $^{13}$C NMR (D$_2$O-Pyr-d$^5$) 178.1, 176.3, 142.7, 135.7, 57.0, 34.7, 31.5, 29.8, 16.5. IR (KBr) 3447, 1671, 1593, 1533, 1402, 1262 cm$^{-1}$. Anal. (C$_9$H$_{15}$NO$_4$S.H$_2$O) C, H, N.

(2S,4E)-2-Amino-4-carboxy-5-propylpent-4-enoic acid $[\alpha]_D$=+36.3 (c 1, 1N HCl). $^1$H NMR (D$_2$O-Pyr-d$^5$) 7.07 (t, J=6.5 Hz, 1H), 4.17 (dd, J=3.6 and 8.9 Hz, 1H), 3.26 and 3.06 (part AB of an ABX system, JAB=14.7 Hz, JAX=3.6 Hz and JBX=8.9 Hz), 2.48 (c, J=7.3 Hz, 2H), 1.69 (m, 2H), 1.18 (t, J=7.2 Hz, 3H). $^{13}$C NMR (D$_2$O-Pyr-d$^5$) 178.6, 176.6, 145.8, 134.1, 57.2, 32.4, 31.5, 24.1, 15.6. IR (KBr) 3400, 1699, 1589, 1526, 1350, 1219 cm$^{-1}$. Anal. (C$_9$H$_{15}$NO$_4$.H$_2$O) C, H, N.

(2S,4E)-2-Amino-4-carboxy-6-methylhept-4-enoic acid

Mp>200° C.; $[\alpha]_D$=−22.0 (c 0.2, Py). $^1$H NMR (D$_2$O-Pyr-ds) 6.50 (d, J=10.3 Hz, 1H), 3.75 (dd, J=3.7 and 8.5 Hz, 1H), 3.85 (part A of an ABX system, JAB=14.7 Hz, JAX=3.7 Hz, 1H), 2.72–2.50 (m, 2H), 0.90 (m, 6H). $^{13}$C NMR (D$_2$O-Pyr-d$^5$) 176.5, 173.9, 149.5, 129.5, 54.9, 29.0, 27.2, 21.5. IR (KBr) 3450, 1686, 1636, 1263 cm$^{-1}$. Anal. (C$_9$H$_{15}$NO$_4$.H$_2$O) C, H, N.

(2S,4Z)-2-Amino-4-carboxy-6-methylhept-4-enoic acid $[\alpha]_D$=+52.0 (c 0. 5, Py). $^1$H NMR (MeOD-KOD) 5.15 (d, J=9.1 Hz, 1H), 3.40–3.25 (m, 1H), 3.00–2.70 (m, 2H), 3.00–2.75 (m, 2H), 2.16 (m, 1H), 1.00 (m, 6H). $^{13}$C NMR (D$_2$O-Pyr-d$^5$) 177.3, 173.6, 141.5, 131.0, 54.5, 35.6, 28.3, 22.0, 21.8. Anal. (C$_9$H$_{15}$NO$_4$.$^{1/2}$H$_2$O) C, H, N.

(2S)-2-Amino-4-carboxy-5-ethylhept-4-enoic acid $[\alpha]_D$=30.0 (c 0.2, Py). $^1$H NMR (MeOH-d$^4$-KOD) 6.45 (s, 1H), 3.25 (m, 1H), 2.85 (dd, J=5.7 and 13.7 Hz, 1H), 2.48 (dd, J=9 and 13.7 Hz, 1H), 1.12 (s, 9H) $^{13}$C NMR (MeOH-d$^4$-KOD) 182.7, 178.7, 147.0, 136.8, 57.4, 35.9, 33.7, 31.8. Anal. (C$_{10}$H$_{17}$NO4.H$_2$O) C, H, N.

(2S,4E)-2-Amino-4-carboxy-7-methyloct-4-enoic acid

Mp 190–199° C. $[\alpha]_D$=+14.0 (C 0.5, Py). $^1$H NMR (D$_2$O-Pyr-d$^5$) 6.53 (m, 1H), 3.57 (m, 1H), 2.72 (m, 1H), 2.48 (m, 1H), 1.85 (m, 2H), 1.40 (m, 1H), 0.60 (m, 6H). $^{13}$C NMR (D$_2$O-Pyr-d$^5$) 176.0, 173.9, 142.1, 132.0, 54.6, 36.6, 28.9, 27.6, 21.5, 21.4. Anal. (C$_{10}$H$_{17}$NO$_4$.H$_2$O) C, H, N.

(2S, E)-2-amino-4-(4,4-diphenylbutylidene)pentanedioic acid, hydrochloride

75% Yield. White solid, m.p. 155–7° C. (dec). $[\alpha]_D$=+17.0 (c 0.5, DMSO). $^1$H NMR (MeOH-d$^4$) 7.40–7.00 (m, 10H), 3.94 (m, 1H), 3.85 (dd, J=6.3 and 7.6 Hz, 1H), 2.77 and 2.61 (part AB of ABX system, J$_{AB}$=14.3 Hz, J$_{AX}$=6.3 Hz, $J_{BX}$=7.6 Hz, 2H), 2.40–2.10 (m, 4H). $^{13}$C NMR (MeOH-d$^4$) 171.4, 170.5, 148.5, 145.8, 129.6, 128.9, 127.8, 127.3, 53.7, 52.1, 35.3, 29.1, 28.4. IR (KBr pellet) 3428, 3300–2200 (CO$_2$H), 1690, 1219 cm$^{-1}$.

(2S, Z)-2-amino-4-(4,4-diphenylbutylidene) pentanedioic acid, hydrochloride

70% Yield. White solid, m.p. 196–8° C. (dec). $[\alpha]_{D}$=+46.0 (c 0.5, DMSO). $^1$H NMR (D$_2$O/KOD/MeOH-d$^4$) 7.45–7.15 (m, 10H), 5.39 (m, 1H), 3.99 (m, 1H), 3.23 (dd, J=3.5 and 10.0 Hz, 1H), 2.76 (dd, J=3.5 and 13.9 Hz, 1H), 2.32–2.00 (m, 5H). $^{13}$C NMR (D$_2$O/KOD/MeOH-d$^4$) 183.1, 179.2, 146.5, 146.4, 137.9, 131.6, 129.7, 128.9, 128.8, 127.3, 56.0, 51.4, 42.6, 35.8, 28.8. IR (KBr pellet) 3430, 3300–2200 (CO$_2$H), 1699, 1630, 1252 cm$^{-1}$.

(2S)-2-Amino-4-cyclobutylidenepentanedioic acid

M.p.: 212–214° C. $[\alpha]_{D}$=+5.0 (c 0.2, 1N HCl) .$^1$H NMR (MeOH-d$_4$/KOD) 3.27 (dd, 1H, J=8.9 and 4.2 Hz, H-2), 3.00 (q, 2H, J=7.2 Hz), 2.77 (t, 2H, J=7.6 Hz), 2.59 (dd, 1H, J=13.2 and 4.2 Hz), 2.20 (dd, 1H J=13.2 and 8.9 Hz), 1.93 (quintuplet, 2H, J=7.6 Hz). $^{13}$C NMR (MeOH-d$_4$/KOD) 183.0, 176.9, 152.2, 128.8, 57.2, 36.8, 34.0, 31.7, 17.7. IR (KBr) 2915, 1663, 1632, 1595, 1308 cm$^{-1}$. Anal. (C$_9$H$_{13}$NO$_4$.$^{1/2}$H$_2$O) C, H, N.

(2S)-2-Amino-4-cyclopentylidenepentanedioic acid

M.p.: 205° C. $[\alpha]_{D}$=−22.0 (c 0.5 , DMSO). $^1$H NMR (D$_2$O-Pyr-d$^5$) 4.22 (dd, J=3.5 and 10.6 Hz, 1H), 3.32 (dd, J=3.6 and 14.0 Hz, 1H), 3.10–2.60 (m, 5H), 2.0–1.65 (m, 4H). $^{13}$CNMR (D$_2$O-Pyr-d$^5$) 179.40, 176.6, 157.4, 126.0, 56.7, 35.5, 35.4, 33.8, 28.6, 27.6. IR (KBr) 3410, 3090, 1713, 1660, 1624, 1410, 1178 cm$^{-1}$. Anal. (C$_{10}$H$_{15}$NO$_4$.2H$_2$O) C, H, N.

(2S,E)-2-Amino-4-[(2,2-dimethyl)cyclopentylidene] pentanedioic acid hydrochloride $^1$H NMR (MeOH-d$^4$-KOD) 4.04 (m, 1H), 3.44 (m, 1H), 2.56 (m, 1H), 2.40–2.10 (m, 4H), 1.81 (m, 2H), 1.12 (s, 6H).$^{13}$C NMR (MeOH-d$^{4-}$KOD) 179.1, 173.2, 148.9, 128.8, 52.9, 47.6, 41.5, 41.2, 34.2, 30.1, 27.4, 27.1. IR (KBr) 3400, 1760, 1750, 1625, 1230 cm$^{1-}$.

(2S,Z)-2-Amino-4-[(2,2-dimethyl)cyclopentylidene] pentanedioic acid hydrochloride $^1$H NMR (MeOH-d$^4$-KOD) 4.13 (m, 1H), 3.22 (m, 1H), 3.05 (m, 1H), 2.81 (m, 2H), 1.69 (m, 4H), 1.30 (s, 3H), 1.27 (s, 3H). $^{13}$C NMR (MeOH-d$^{4-}$KOD) 171.15 (2C), 119.6, 111.9, 54.1, 45.9, 45.2, 37.9, 31.4, 27.9 (2C), 23.8. IR 1733, 1717 cm$^{-1}$.

(2S,4E)-2-Amino-4-carboxy-5-cyclopropylpent-4-enoic acid

Mp 204° C. $[\alpha]$hd D=+32.9 (c 1 , 1N HCl). $^1$H NMR (D$_2$O-Pyr-d$^5$) 6.50 (d, J=10.0 Hz, 1H), 4.30 (dd, J=4.0 and 9.1 Hz, 1H), 3.46 and 3.18 (part AB of an ABX system, JAB=14.8 Hz, JAX=4.0 Hz and JBX=9.1 Hz), 2.05 (m, 1H), 1.24 (m, 2H), 0.9 (m, 2H). 13C NMR (D$_2$O-Pyr-d$^5$) 178.0, 176.5, 151.1, 131.2, 57.4, 31.7, 13.4, 10.5. IR (KBr) 3420, 1721, 1657, 1632, 1412, 1123 cm$^{-1}$. Anal. (C$_9$H$_{13}$NO$_4$.H$_2$O) C, H, N.

(2S,E)-2-Amino-4-cyclopentylmethylidenepentanedioic acid

M.p.: 173–175° C. $[\alpha]_{D}$=+23.0 (c 0.1, 1N HCl).$^1$H NMR (MeOH-d$_4$/KOD) 6.45 (d, 1H, J=10.0 Hz, HC═), 3.28 (m, 1H, H-2), 2.83 (m, 1H), 2.78 (dd, 1H, J=13.4 and 4.8 Hz), 2.45 (dd, 1H, J=13.4 and 9.3 Hz), 1.87–1.58 (m, 6H), 1.37–1.22 (m, 2H). $^{13}$C NMR (MeOH-d$_4$/KOD) 182.7, 177.5, 144.6, 135.2, 57.5, 40.4, 35.6, 34.6 (2C), 26.6 (2C). IR (KBr) 2928, 1705, 1658, 1604, 1400 cm$^{-1}$. Anal. (C$_{11}$H$_{17}$NO$_4$.H$_2$O) C, H, N.

(2S,4E)-2-Amino-4-carboxy-5-cyclohexylpent-4-enoic acid

M.p.: 205° C. $[\alpha]_{D}$=+32.0 (c 1, 1N HCl). $^1$H NMR (D$_2$O-Pyr-d$^5$) 6.92 (d, J=10.3 Hz, 1H) 4.25 (m, 1H), 3.40 (m, 1H), 3.12 (m, 1H), 2.73 (m, 1H) 2.0–1.15 (m, 10H). $^{13}$C NMR (D$_2$O-Pyr-d$^5$) 178.4, 176.2, 150.4, 132.0, 57.5, 39.1, 34.1, 34.0, 31.6, 27.6, 27.2, 27.0. IR (KBr) 3500, 1688, 1584, 1496, 1300 cm$^{-1}$. Anal. (C$_{12}$H$_{19}$NO$_4$.H$_2$O) C, H, N.

(2S,4E,6E)-2-Amino-4-carboxyocta-4,6-dienoic acid

M.p.: 190° C. $[\alpha]_{D}$=+37.0 (c 0.5, DMSO). $^1$H NMR (D$_2$O-Pyr-d$^5$) 7.46 (d, J=11.2 Hz, 1H), 6.78 (m, 1H), 6.42 (dq, J=6.8 and 14.4 Hz, 1H), 4.15 (dd, J=3.6 and 9.0 Hz, 1H), 3.33 and 3.11 (part AB of an ABX system, JAB=14.4 Hz, JAX=3.6 Hz and JBX=9.0 Hz, 2H), 2.14 (d, J=6.8 Hz, 3H). $^{13}$C NMR (D$_2$O-Pyr-d$^5$) 178.8, 176.4, 141.7, 141.2, 130.8, 128.8, 57.1, 31.5, 20.4. IR (KBr) 3426, 3034, 1684, 1641, 1242 cm$^{-1}$.

(2S,E)-2-Amino-4-anthrylidenepentanedioic acid

M.p.: 167–269 C. $[\alpha]_{D}$=+55.7 (c 0.35, DMSO).$^1$H NMR (MeOH-d$_4$/KOD) 8.35–8.29 (m, 1H), 8.11–7.98 (m, 4H), 7.52–7.41 (m, 4H), 3.34 (dd, 1H, J=10.6 and 2.3 Hz, H-2), 2.84 (dd, 1H, J=13.2 and 2.3 Hz), 1.96 (dd, 1H, J=13.2 and 10.6 Hz). $^{13}$C NMR (MeOH-d$_4$/KOD) 187.8, 176.2, 144.1, 133.0, 132.8, 132.6, 131.1, 130.1, 129.9, 129.8, 127.3, 127.0, 126.9, 126.8, 126.4, 126.3, 56.5, 38.3. IR (KBr) 3435, 1678, 1622, 1238 cm$^{-1}$. Anal. (C$_{20}$H$_{16}$NO$_4$.2H$_2$O) C, H, N.

(2S, E, E) -2-Amino-4-(2-methoxycinnamylidene) pentanedioic acid

M.p.: 187–189° C. $[\alpha]_{D}$=+37.0 (c 0.1, 3N HCl) .$^1$H NMR (MeOH-d$_4$/KOD) 7.17 (d, 1H, J=7.6 Hz), 6.84 (t, 1H, J=7.8 Hz), 6.71–6.68 (m, 3H), 6.58–6.50 (m, 2H), 3.78 (s, 3H, OCH$_3$), 2.84 (dd, 1H, J=9.5 and 4.8 Hz, H-2), 2.38 (dd, 1H J=13.3 and 4.8 Hz), 2.15 (dd, 1H, J=13.3 and 9.5 Hz). $^{13}$C NMR (MeOH- d$_4$/KOD) 183.5, 177.7, 157.7, 138.8, 135.5, 133.0, 131.1, 128.1, 126.7, 126.6, 122.4, 113.1, 57.4, 56.9, 35.1. IR (KBr) 1674, 1595, 1489, 1246 cm$^{-1}$. Anal. (C$_{15}$H$_{17}$NO$_5$.H$_2$O) C, H, N.

EXAMPLE 2

A tablet is prepared using the ingredients below:

| | Quantity (mg/tablet) |
|---|---|
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

EXAMPLE 3

Tablets each containing 60 mg of active ingredient are made as follows:

| | |
|---|---|
| Active Ingredient | 60 mg |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

EXAMPLE 4

Capsules each containing 80 mg medicament are made as follows:

| | |
|---|---|
| Active Ingredient | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 sieve, and filled into hard gelatin capsules in 200 mg quantities.

EXAMPLE 5

Suspensions each containing 50 mg of medicament per 5 ml dose are made as follows:

| | |
|---|---|
| Active Ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

We claim:

1. A compound of the formula:

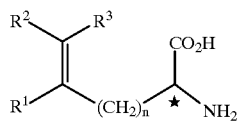

in which n is 1 or 2, $R^1$ is —$CO_2H$,
$R_2$ is hydrogen or $C_{1-4}$ alkyl and $R^3$ is hydrogen, $C_{1-10}$ alkyl, $C_{2-10}$ alkenyl, optionally substituted phenyl, optionally substituted phenyl-$C_{1-4}$ alkyl, optionally substituted phenyl $C_{2-10}$ alkenyl, (optionally substituted phenyl)$_2$-$C_{1-4}$ alkyl, optionally substituted $C_{3-7}$ cycloalkyl, optionally substituted $C_{3-7}$ cycloalkyl-$C_{1-4}$ alkyl or optionally substituted $C_{3-7}$ cycloalkyl-$C_{2-10}$ alkenyl, or $R^2$ and $R^3$, together with the carbon atom to which they are attached, form an optionally substituted $C_{4-7}$ cycloalkyl group; or a salt or ester thereof other than the compounds γ-propylidene-L-glutamic acid, γ-ethylidene-L-glutamic acid and γ-methylidene-L-glutamic acid.

2. A compound according to claim 1 in which n is 1.

3. A compound according to claim 1 which has 2S stereochemistry.

4. A compound according to claim 1 in which n is 1, $R^1$ is —$CO_2H$, $R^2$ is hydrogen and $R^3$ is $C_{1-4}$ alkyl.

5. A compound according to claim 1 wherein $R^3$ is $C_3$ or $C_4$ alkyl.

6. A compound according to claim 1 in which n is 1, $R^1$ is —$CO_2H$, $R^2$ is hydrogen and $R^3$ is $C_{3-4}$ alkyl or branched alkyls such as isopropyl or $R^2$ and $R^3$ together with the carbon atom to which they are attached form an optionally substituted $C_4$ or $C_5$ cycloalkyl.

7. A compound according to claim 1 in which $R^2$ is hydrogen and $R^3$ is $C_{1-4}$ alkyl.

8. A compound selected from
(2S, E, E) -2-Amino-4-(p-nitrocinnamylidene)pentanedioic acid,
(2S, E, E) -2-Amino-4-(p-dimethylaminocinnamylidene) pentanedioic acid,
(2S, E, E) -2-Amino-4-cinnamylidenepentanedioic acid,
(2S, E)-2-Amino-4-pentylidenepentanedioic acid,
(2S) -2-Amino-4-isopropylidenepentanedioic acid,
(2S)-2-Amino-4-cyclobutylidenepentanedioic acid,
(2S, E) -2-Amino-4-(p-chlorophenylmethylidene) pentanedioic acid,
(2S)-2-Amino-4-cyclohexylidenepentanedioic acid
(2S, E) -2-Amino-4-cyclopentylmethylidenepentanedioic acid and
(2S)-2-Amino-4-cyclopentylidenedioic acid.

9. A pharmaceutical formulation comprising a compound according to claim 1, or a pharmaceutically-acceptable salt or ester thereof, together with a pharmaceutically-acceptable diluent or carrier.

10. A process for the production of compounds of formula (1) which comprises hydrolysing a compound of the formula:

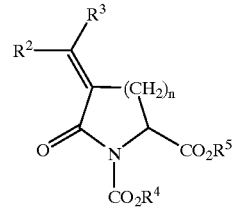

where $R^4$ and $R^5$ are each carboxy protecting groups, to give a compound of formula (I).

11. A compound according to claim 1, or a pharmaceutically-acceptable salt or ester thereof, for use as a pharmaceutical.

12. A method of treating an animal suffering from or susceptible to a disorder of the central nervous system, which comprises administering a compound according to claim 1, or a pharmaceutically acceptable salt or ester thereof.

13. A method according to claim 12, in which the animal is a human.

* * * * *